United States Patent [19]

Kristensson et al.

[11] 4,115,414

[45] Sep. 19, 1978

[54] ESTRAMUSTINE PHOSPHATE ALCOHOL COMPLEXES, THEIR PREPARATION, AND THEIR USE AS INTERMEDIATES IN PURIFICATION OF SAID COMPOUND AND SALTS THEREOF

[75] Inventors: Sten Krister Kristensson; Anders Robert Stamvik, both of Helsingborg, Sweden

[73] Assignee: Aktiebolaget Leo, Sweden

[21] Appl. No.: 773,911

[22] Filed: Mar. 3, 1977

[30] Foreign Application Priority Data

Mar. 10, 1976 [GB] United Kingdom ............... 9451/76

[51] Int. Cl.$^2$ .............................................. C07J 1/00
[52] U.S. Cl. ................................................ 260/397.5
[58] Field of Search ..................................... 260/397.5

[56] References Cited

U.S. PATENT DOCUMENTS

| Re. 29,199 | 5/1977 | Flex et al. | 260/397.5 |
| 3,963,707 | 6/1976 | Hogberg et al. | 260/397.5 |

*Primary Examiner*—Elbert L. Roberts
*Attorney, Agent, or Firm*—Gordon W. Hueschen

[57] ABSTRACT

This invention relates to Estramustine Phosphate alcohol complexes, their preparation, and their use as intermediates in purification of said compound and salts thereof, and more particularly to a method of such purification which involves the use of certain alcohols which form molecular complexes with Estramustine Phosphate. It also includes said novel molecular complexes.

23 Claims, No Drawings

ESTRAMUSTINE PHOSPHATE ALCOHOL COMPLEXES, THEIR PREPARATION, AND THEIR USE AS INTERMEDIATES IN PURIFICATION OF SAID COMPOUND AND SALTS THEREOF

This invention relates to Estramustine Phosphate alcohol complexes, their preparation, and their use as intermediates in purification of said compound and salts thereof, and more particularly to a method of such purification which involves the use of certain alcohols which form molecular complexes with Estramustine Phosphate. It also includes said novel molecular complexes.

BACKGROUND OF THE INVENTION

The compound estradiol-3-N-bis($\beta$-chloroethyl)-carbamate-17$\beta$-dihydrogen phosphate has been found to be very useful as an antitumour agent in the clinic (see e.g. Cancer Chemotherapy Reports Part 1, vol. 59, No. 1, 1975). This compound is designated as Estramustine Phosphate herein, this being its generic name and the established INN name. (Recommended International Non-Proprietary Name.)

The compound is presently used in the clinic either as its N-methylglucamine salt or as its disodium salt depending on the way of administration (intravenously or orally).

A method for the synthesis of antitumour compounds, having a structure derived from estradiol-17-dihydrogen phosphate, is described and claimed in British Pat. No. 1,016,959. In Example 15 of its specification, the preparation of Estramustine Phosphate is described. According to this example, said compound has been isolated by pouring its crude pyridinum salt into an excess of hydrochloric acid. The precipitate obtained is collected and washed with 0.1 N hydrochloric acid and water. The compound obtained is said to melt with decomposition at about 155° C, to have an $[\alpha]_D^{20°C} = +30.0°$ (c = 1.0 in dioxane), and to be soluble in an aqueous solution of alkali.

It has now been found that the compound obtained according to said example is not pure and, inter alia, always contains at least 3–4% and mostly more than 5% of pyridine as an impurity. This content of pyridine is only slightly reduced by repeated reprecipitations of the phosphate ester from alkaline solutions with hydrochloric acid — operations which also are very difficult to perform as the free acid under such conditions is precipitated in a jelly-like form which makes it practically impossible to collect and wash.

Estramustine Phosphate and salts thereof may also contain degradation products such as estradiol-17-dihydrogen phosphate and its corresponding salts.

As far as the salts of Estramustine Phosphate are concerned, it has been found that said impurities are practically impossible to remove by recrystallization. To purify such an impure free acid, repeated recrystallizations from mixtures of ethanol-hexane can be used, but result in a very low yield of the pure acid.

It has now been found that impure Estramustine Phosphate can be purified by conversion to a molecular complex as by crystallization from a medium containing an alcohol having at least three carbon atoms, whereby said molecular complex formed is an addition compound between the pure acid and the alcohol used.

Although no theoretical upper limit for the number of carbon atoms in the alcohol exists, in general a maximum of eight carbon atoms represents the upper limit imposed by certain practical limitations such as melting points and boiling points.

It has also been found that impure salts of Estramustine Phosphate can be purified by converting said salts to said pure complexes. These complexes are stable compounds which can subsequently be dissolved in a solvent other than the type of solvent employed in its preparation with resulting precipitation of pure Estramustine Phosphate itself, or they may be dissolved in a suitable solvent in the presence of a suitable source of sodium to precipitate out a pure Estramustine Phosphate sodium salt. The source of the starting impure Estramustine Phosphate may be the free acid itself or any salt thereof which can readily be converted to the starting Estramustine Phosphate free acid by acidification.

Pure Estramustine Phosphate and its pure salts are obtained in high yields from said complexes by crystallization from suitable solvents or mixtures thereof.

SUMMARY OF THE INVENTION

The invention, in one of its tangible embodiments, consists in novel Estramustine Phosphate alcohol complexes, wherein the alcohol has at least three carbon atoms and is selected from the group consisting of alkanols and cycloalkanols, preferably wherein the Estramustine Phosphate and the alcohol are present in a 1:1 molar ratio and preferably where the alcohol contains up to a maximum of eight carbon atoms.

In a second tangible embodiment of the invention, it comprises a process for the purification of Estramustine Phosphate or a salt thereof involving the formation of an alcohol complex of Estramustine Phosphate by dissolving Estramustine Phosphate in the presence of an alcohol having at least three carbon atoms selected from the group consisting of alkanols and cycloalkanols in liquid phase and precipitating the Estramustine Phosphate alcohol complex from solution.

A further tangible embodiment of the present invention comprises dissolving said Estramustine Phosphate alcohol complex in a solvent other than an alcohol as defined above and then precipitating the purified Estramustine Phosphate therefrom.

In an additional tangible embodiment of the present invention, it comprises a process of dissolving the Estramustine Phosphate alcohol complex in an organic solvent and precipitating an Estramustine Phosphate sodium salt therefrom by reacting therewith in solution sodium hydroxide, sodium alcoholate, or a sodium salt of a weak acid.

Other tangible embodiments of the invention will become apparent hereinafter and will be illustrated specifically in the examples and still others will be apparent to one skilled in the art to which this invention pertains.

THE NOVEL ESTRAMUSTINE PHOSPHATE COMPLEXES

The novel molecular complexes have the general formula

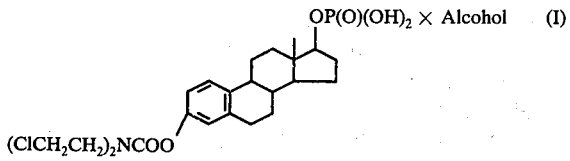

wherein as previously stated the alcohol has at least three and preferably three through eight carbon atoms and is an alkanol or a cycloalkanol.

Although it is possible to employ all kinds of alcohols, having at least three carbon atoms, to form the complex of the formula (I), it is preferred that the alcohol has up to a maximum of eight carbon atoms and is an alkanol such as: propan-1-ol, propan-2-ol, butan-1-ol, butan-2-ol, 2-methylpropan-1-ol, 2-methylpropan-2-ol, pentan-1-ol, pentan-2-ol, pentan-3-ol, 2-methylbutan-1-ol, 2-methylbutan-2-ol, 3-methylbutan-1-ol, 3-methylbutan-2-ol, 2,2-dimethylpropan-1-ol, hexan-1-ol, hexan-2-ol, hexan-3-ol, 3,3-dimethylbutan-2-ol, 2-ethylbutan-1-ol, heptan-1-ol, heptan-2-ol, heptan-3-ol, heptan-4-ol, 2,4-dimethylpentan-3-ol, 3-ethylpentan-3-ol, octan-1-ol, octan-2-ol, 4-methylheptan-3-ol, and 2-ethylhexan-1-ol; or a cycloalkanol such as: cyclopentanol, cyclohexanol, 2-methylcyclohexanol, 3-methylcyclohexanol, 4-methylcyclohexanol, and 2-ethylcyclohexanol, the alcohols having a maximum of six carbon atoms being especially preferred.

Particularly preferred alkanols which form addition compounds with Estramustine Phosphate in the form of stable 1:1 molecular complexes are branched alkanols and especially secondary and tertiary alkanols such as: propan-2-ol, butan-2-ol, 2-methylpropan-1-ol, 2-methylpropan-2-ol, pentan-2-ol, pentan-3-ol, 2-methylbutan-1-ol, 2-methylbutan-2-ol, 3-methylbutan-1-ol, 3-methylbutan-2-ol, 2,2-dimethylpropan-1-ol, hexan-2-ol, hexan-3-ol, 3,3-dimethylbutan-2-ol, 2-ethylbutan-1-ol, heptan-2-ol, heptan-3-ol, 2,4-dimethylpentan-3-ol, 3-ethylpentan-3-ol, octan-2-ol, 4-methylheptan-3-ol, and 2-ethylhexan-1-ol. Especially preferred alkanols are propan-2-ol, butan-2-ol, and 2-methylpropan-2-ol. The most preferred cycloalkanol is cyclohexanol.

Procedure for preparing pure complexes having the general formula (I) from impure Estramustine Phosphate Impure Estramustine Phosphate, either undried or dried, is converted into its pure molecular complex having the general formula (I) above by crystallization from a medium containing at least that amount of the alcohol necessary to form said complex. An excess of alcohol is usually employed.

The crystallization medium may contain, besides one or more of the alcohols as defined above, also water and another organic solvent such as methanol, ethanol, acetonitrile; a lower alkyl ester of a lower alkanoic acid, e.g., methyl acetate, ethyl acetate, or butyl acetate; ethers, e.g., dioxane or tetrahydrofurane; ketones, e.g., acetone, methyl isobutyl ketone or methyl ethyl ketone; or the like.

If the crude Estramustine Phosphate contains pyridine as an impurity, it has been found suitable to add an amount of hydrochloric acid or other strong mineral or organic acid, corresponding to the pyridine content of the crude Estramustine Phosphate acid, to the crystallization medium, as such an addition increases the yield of the complex or mixture of complexes obtained, by binding the pyridine by forming the pyridinium salt thereof.

If the crystallization medium contains water, it is preferred that the concentration of the alcohol by volume in the medium be at least the same and preferably twice the concentration of water. If water is the only solvent besides the alcohol, it is preferred to use a secondary or tertiary alcohol.

It is preferred that the crystallization medium contain only a single alcohol, and optionally water and hydrochloric acid, so that an individual defined complex is obtained.

The temperature employed during this purification process may be anywhere between about 150° C and the freezing point of the medium, preferably between −20° C and 100° C. Room temperature is suitable.

Although the normal procedure is to dissolve the crude acid at a higher temperature, and then cool to room temperature or below to effect crystallization, it has been found possible to perform both the dissolution and crystallization at room temperature.

Procedure for preparing pure complexes having the general formula (I) from impure Estramustine Phosphate salts.

Impure salts of Estramustine Phosphate, either undried or dried, can be transformed into their pure molecular complexes having the general formula (I) by a procedure comprising (a) converting said salt to the free acid and (b) converting said free acid to a said pure complex, whereby these two operations may be performed in one or two steps and in such a way that the complex crystallizes from a crystallization medium containing at least an amount of the alcohol necessary to form said complex.

In the two-step procedure, the salt is suspended or dissolved in water containing at least two equivalents of a strong mineral or organic acid having an anion which forms a water soluble salt with the cation of said Estramustine Phosphate salt, and a water immiscible organic solvent in which the free acid of Estramustine Phosphate is soluble, resulting in an organic phase containing the crude free acid. This free acid is then converted to the complex (I) as described for the free acid, either by direct use of the organic phase as such or after evaporation of the solvent.

Preferred solvents for this operation are lower alkyl esters of lower alkanoic acids, i.e., a lower-alkyl lower-alkanoate, especially methyl acetate or ethyl acetate; chlorinated aliphatic hydrocarbons, e.g., methylene chloride or chloroform; or aliphatic ketones, e.g., methyl isobutyl ketone or methyl ethyl ketone.

All of these operations may be conducted conveniently at room temperature, although higher or lower temperatures may be employed.

In the one-step procedure, the salt is suspended or dissolved in the same kind of medium as described for preparation of the Estramustine Phosphate complex with the addition of a strong mineral or organic acid, having an anion which forms a salt with the cation of said Estramustine Phosphate salt which resulting salt is soluble in the medium employed, thereby freeing up the Estramustine Phosphate for formation of the complex (I). Preferably at least two equivalents of the strong acid are employed where the impure disodium salt is used as starting material.

If the impure salt is a readily water soluble salt of Estramustine Phosphate such as the disodium salt or the N-methylglucamine salt, it is also possible to perform this procedure in two stages, whereby said salt is dissolved to a high concentration in water and this solution then added to the crystallization medium provided that the final amount of alcohol by volume is at least the same and preferably twice the amount of water, resulting in the formation of the pure complex (I). In this two stage operation, secondary and tertiary alcohols are preferred.

When the impure salt of Estramustine Phosphate is an alkali metal salt such as the disodium salt, or an amine salt such as the N-methylglucamine salt, suitable strong mineral acids to be employed in their conversion to the pure complex (I) are such as hydrochloric acid and sulfuric acid, preferably hydrochloric acid.

All the above operations may be conducted conveniently at room temperature, although higher or lower temperatures may be employed.

Procedure for preparing pure Estramustine Phosphate and salts thereof from complexes having the formula (I).

The free acid is readily obtained in pure form from the molecular complex by crystallization from a suitable organic solvent or solvent mixtures excluding alcohols having three or more carbon atoms. This can, e.g., be done by dissolving the complex in warm ethanol from which Estramustine Phosphate crystallizes on cooling. This compound is pure after drying. The solvent should obviously not be one which is of the type used for preparation of the Estramustine Phosphate alcohol complex.

Examples of other solvents which can be used are methanol; acetonitrile; lower alkyl esters of lower-alkanoic acids such as ethyl acetate; ketones such as acetone; ethers such as dioxane and tetrahydrofuran; or the like. Said organic solvents or mixtures thereof may contain water if preferred. Examples of solvents where an addition of at least about the same volume of water is preferred acetone, dioxane, and tetrahydrofurane.

The said molecular complex of Estramustine Phosphate with an alcohol can also be transformed into the pure disodium salt of Estramustine Phosphate by dissolving the complex in a suitable organic solvent containing at least two equivalents of sodium, e.g., in the form of a sodium alcoholate or sodium hydroxide. Any sodium alcoholate suitable for provision of the necessary sodium may be employed. It is also possible to dissolve the complex in one organic solvent and then pour this solution into the same or another organic solvent containing the necessary amount of sodium. Said organic sovents may contain water if such mixtures are preferred, which frequently results in a pure hydrate of said disodium salt, in which hydrated form Estramustine Phosphate disodium salt has been clinically employed from the very beginning.

If an ethanol solution of a complex (I) is poured into an ethanol solution containing at least two equivalents of sodium in any form, but preferably in the form of any of numerous sodium alcoholates, preferably sodium methylate or sodium ethylate, or sodium hydroxide, the disodium salt of Estramustine Phosphate precipitates as a hydrate and can be readily isolated, e.g., by filtration.

Examples of other solvents which can be used are such as ethers, e.g., dioxane or tetrahydrofurane; lower alkylalkanoates, e.g., ethyl acetate; chlorinated aliphatic hydrocarbons e.g., chloroform or methylene chloride; or the like.

To obtain the monosodium salt of Estramustine Phosphate, the complex (I) is preferably reacted in solution with at least one equivalent of the sodium salt of a weak organic acid which is soluble in the solvent employed. Suitable solvents or solvent mixtures are those already mentioned for preparation of the disodium salt. Examples of suitable sources of sodium to precipitate out the pure monosodium salt of Estramustine Phosphate are the sodium salts of alkanoic acids such as the sodium salt of 2-ethylhexanoic acid.

Other acid or neutral salts with different metals may be obtained in the manner described for the mono- and disodium salts.

In this disclosure, the expression "lower" means that the group referred to contains one to four carbon atoms, inclusive. Thus, lower-alkyl and lower-alkanoic acid include: methyl, ethyl, propyl, isopropyl, butyl, secondary butyl, isobutyl, tertiary butyl, methanoic acid, ethanoic acid, propanoic acid, butanoic acid, and 2-methylpropanoic acid.

The purification procedures described in the following examples, being within the scope of the present invention, are of particular interest for the intended purposes. The examples are intended to illustrate but not to limit the scope of the invention. Examples of the novel molecular complexes are described in Example 1 below.

EXAMPLE 1

1.0 kg of crude Estramustine Phosphate obtained according to Example 15 of the British Pat. No. 1,016,959 and containing 4.5% pyridine is added, while agitating, to 10 liters of propan-2-ol at a temperature of about 70° C. As soon as a clear solution is obtained, 0.07 liters of concentrated hydrochloric acid is added, whereupon the solution is cooled to about 10° C while agitating. The pure molecular complex between Estramustine Phosphate and propan-2-ol crystallizes from the solution. It is collected by filtration, washed with 2 liters of cold propane-2-ol and dried at 40° C, yield 0.97 kg. The compound has no defined melting point, it starts to sinter at about 105° C and melts with decomposition at about 170° C.

According to the analytical results (using thin-layer chromatography (TLC), gas chromatography (GC), Nuclear Magnetic Resonance (NMR), and elementary analysis) the compound consists of a stable molecular complex between one mole of pure Estramustine Phosphate and one mole of propan-2-ol. It contains no trace of pyridine. Its content of propan-2-ol, according to GC, is 10.5% (theoretically 10.35%).

The NMR data obtained for this molecular complex are as follows: 0.75 – 2.6 (m,22H) with 0.83 (s,3H) and 1.13 (d,6H), 2.82 (m,2H), 3.5 – 4.6 (m,10H) with 3.75 (broad s,8H), 6.8 – 7.05 (m,2H), 7.3 (d,1H), and 7.9 (s,3H).

In substantially the same manner but replacing propan-2-ol in the above example by the alcohols mentioned in the table below, the following pure stable molecular complexes between one mole of Estramustine Phosphate and one mole of said alcohol are obtained. Their purity is established using TLC, GC, NMR, and elementary analysis.

Table

Isolated pure molecular complexes between one mole of pure Estramustine Phosphate and one mole of alcohol.

| Alcohol | Alcohol content in the complex according to GC | |
|---|---|---|
| | Found | Theoretical |
| Propan-1-ol | 10.6% | 10.35% |
| Butan-1-ol | 12.2% | 12.47% |
| Butan-2-ol | 12.6% | " |
| 2-Methylpropan-1-ol | 12.5% | " |
| 2-Methylpropan-2-ol | 12.3% | " |
| Pentan-1-ol | 14.6% | 14.49% |
| Pentan-2-ol | 14.5% | " |
| 2-Methylbutan-1-ol | 14.3% | " |
| 3-Methylbutan-1-ol | 14.7% | " |
| 2-Methylbutan-2-ol | 14.6% | " |
| 3-Methylbutan-2-ol | 14.4% | " |
| Pentan-3-ol | 14.7% | " |
| 2,2-Dimethylpropan-1-ol | 14.6% | " |
| Hexan-1-ol | 16.5% | 16.42% |
| Hexan-2-ol | 16.1% | " |
| Hexan-3-ol | 16.2% | " |
| 3,3-Dimethylbutan-2-ol | 16.6% | 16.42% |
| 2-Ethylbutan-1-ol | 16.0% | " |
| Heptan-2-ol | 18.0% | 18.25% |
| 2,4-Dimethylpentan-3-ol | 18.1% | " |
| Octan-1-ol | 19.8% | 20.00% |
| Octan-2-ol | 20.0% | " |
| Cyclohexanol | 15.5% | 15.40% |

In substantially the same manner, but replacing propan-2-ol in the above example by ethyl acetate:propan-2-ol(15:2), ethanol:propan-2-ol(50:40), methanol:propan-2-ol(50:50), acetone:propan-2-ol(50:50), methyl isobutyl ketone:propan-2-ol(50:50), dioxane:propan-2-ol(50:50), the same propan-2-ol complex of Estramustine Phosphate is obtained.

Also, in substantially the same manner, but replacing the crude Estramustine Phosphate in the above example by the butan-1-ol complex of Estramustine Phosphate (prepared as shown above), the same propan-2-ol complex is obtained.

Furthermore, in substantially the same manner, but employing room temperature and replacing the propan-2-ol in the above example by propan-2-ol:water(70:30), propan-2-ol: water(55:45), butan-2-ol:water(70:30), or 2-methylpropan-2-ol:water(70:30), the corresponding complexes are obtained (as prepared and shown above).

The solvent ratios given above are all by volume.

EXAMPLE 2

22 g of crude disodium salt of Estramustine Phosphate is suspended in 100 ml of ethyl acetate. Then 20 ml of 5-M hydrochloric acid is added, whereby the product is dissolved and two clear phases are obtained. The ethyl acetate phase is collected and washed with water. The ethyl acetate solution, containing the Estramustine Phosphate, is poured into 300 ml of propan-2-ol. A precipitate is formed which is collected by filtration, washed with 40 ml of propan-2-ol and dried at 40° C. The yield is about 18.6 g. The compound obtained is the molecular complex between one mole of pure Estramustine Phosphate and one mole of propan-2-ol (as established by TLC, GC, and NMR).

In substantially the same manner, but replacing the ethyl acetate by butyl acetate, methyl isobutyl ketone, or methyl ethyl ketone, the same propan-2-ol complex is obtained.

Also, in substantially the same manner, but replacing the propan-2-ol in the above example by 2-methylpropan-2-ol, butan-2-ol, or cyclohexanol, the same complexes with said alcohols are obtained, as prepared in Example 1 and shown in the table therein.

Furthermore, in substantially the same manner, but replacing the crude disodium salt of Estramustine Phosphate by a crude monosodium salt of Estramustine Phosphate, the same propan-2-ol complex of Estramustine Phosphate is obtained.

EXAMPLE 3

5.6 of crude disodium salt of Estramustine Phosphate is dissolved in 25 ml of water. The solution is then poured, while agitating, into a solution of 2.5 ml of concentrated hydrochloric acid in 125 ml of 2-methylpropan-2-ol. A precipitate is formed which is collected by filtration, washed with 20 ml of 80% 2-methylpropan-2-ol and dried at 40° C. The compound obtained is the molecular complex between one mole of pure Estramustine Phosphate and one mole of 2-methylpropan-2-ol (as established by TLC, GC, NMR).

In substantially the same manner, but replacing the 2-methylpropan-2-ol by propan-2-ol, butan-2-ol, or butan-1-ol, the same complexes are obtained as prepared in Example 1.

Also, in substantially the same manner, but replacing the crude disodium salt of Estramustine Phosphate by a crude N-methylglucamine salt of Estramustine Phosphate, the same propan-2-ol complex as obtained above is prepared.

EXAMPLE 4

5.6 g of crude disodium salt of Estramustine Phosphate is suspended in 100 ml of chloroform. 5 ml of 5-M hydrochloric acid is added, while agitating, whereby the product is dissolved and two clear phases are obtained. The chloroform phase is collected, washed with water, and most of the chloroform is stripped in vacuo. The residue is dissolved in 50 ml of 3-methylbutan-1-ol at about 50° C and then cooled. The precipitate obtained is collected by filtration, washed with 10 ml of cold 3-methylbutan-1-ol, and dried in vacuo at 40° C. The obtained yield is 4.3 g. The compound obtained is a molecular complex between one mole of pure Estramustine Phosphate and one mole of 3-methylbutan-1-ol (as established by TLC, GC, NMR).

In substantially the same manner, but replacing chloroform in the above example by methylene chloride, the same 3-methylbutan-1-ol complex is obtained.

EXAMPLE 5

300 g of the propan-2-ol complex of Estramustine Phosphate (prepared according to Example 1) is dissolved in 1.2 liters of ethanol at about 40° C while agitating. When cooled to 0° C the Estramustine Phosphate crystallizes. It is collected by filtration, washed with 50 ml of cold ethanol, and dried in vacuo at 40° C. The yield is 240 g. The product obtained is pure Estramustine Phosphate according to TLC, GC, and NMR.

In substantially the same manner as in the above example, all the other complexes given in Example 1 are converted to the pure Estramustine Phosphate, according to TLC, GC, and NMR.

Also, in substantially the same manner, but replacing the ethanol by ethyl acetate, acetonitrile, acetone:ethyl acetate(1:3), methanol:water(3:2), acetone:water(1:1), dioxane:water(1:1), or tetrahydrofurane:water(1:1), pure Estramustine Phosphate is obtained.

The solvent ratios given above are by volume.

EXAMPLE 6

110 g of the propan-2-ol complex of Estramustine Phosphate (prepared according to Example 1) is dissolved in 1 liter of ethanol. This solution is slowly added to a solution of 27 g of sodium methylate in 0.8 liters of ethanol, while agitating, and at a temperature of about 20° C. The precipitated product is collected by filtration, washed with 200 ml of ethanol and dried at 35° C. The compound obtained is the pure disodium salt of Estramustine Phosphate, as a hydrate (as established by TLC, NMR, Karl Fisher titration, and elementary analysis).

In substantially the same manner as in the above example, all the other complexes given in Example 1 are converted to the same disodium salt of Estramustine Phosphate.

Also, in substantially the same manner, but replacing sodium methylate in the above example by sodium ethylate or sodium hydroxide, the same disodium salt of Estramustine Phosphate is obtained.

Furthermore, in substantially the same manner, but replacing the ethanol employed for dissolving the complex in the above example by methyl acetate or chloroform, the same disodium salt of Estramustine Phosphate is obtained. Also, by replacing all ethanol employed in the above example by dioxane, the same salt is obtained.

All solvents employed in this example are non-anhydrous.

EXAMPLE 7

29 g of the propan-2-ol complex of Estramustine Phosphate (prepared according to Example 1) is dissolved in 300 ml of ethanol. The solution is heated to 60° C and added to a mixture of 62 ml 1.2-M aqueous sodium 2-ethylhexanoate solution and 240 ml of ethanol. The addition is performed at 60° C while agitating vigorously. After the addition is completed, the solution is kept at 50° C for 15 minutes, and then cooled to 30° C. The obtained precipitate is collected by filtration and washed with 100 ml of ethanol. After drying in vacuo at 40° C, a yield of 23.3 g is obtained. The product obtained is the monosodium salt of Estramustine Phosphate (as established by TLC, NMR, and elementary analysis).

We claim:

1. In a process for the purification of Estramustine Phosphate or a salt thereof, the step of forming an alcohol complex thereof by dissolving Estramustine Phosphate in the presence of an alcohol having at least three carbon atoms selected from the group consisting of alkanols and cycloalkanols in liquid phase and precipitating the Estramustine Phosphate alcohol complex from solution.

2. Process of claim 1, wherein the alcohol has a maximum of eight carbon atoms.

3. Process of claim 2, wherein the Estramustine Phosphate alcohol complex formed has a molar ratio of 1:1.

4. Process of claim 3, wherein the alcohol is selected from the group consisting of secondary and tertiary alcohols.

5. Process of claim 4, wherein the alcohol is selected from the group consisting of propan-2-ol, butan-2-ol, 2-methylpropan-2-ol and cyclohexanol.

6. Process of claim 2, wherein the starting Estramustine Phosphate contains a salt with pyridine as an impurity and wherein a strong acid is added to bind the pyridine by forming a salt therewith.

7. Process of claim 6, wherein the strong acid is hydrochloric acid.

8. Process of claim 2, wherein the complex formation is carried out at room temperature in the presence of water.

9. Process of claim 2, wherein the starting material is a water-soluble salt of Estramustine Phosphate and wherein a strong acid is employed to convert the Estramustine Phosphate salt to the Estramustine Phosphate.

10. Process of claim 9, wherein the water-soluble salt is a disodium salt or a N-methylglucamine salt of Estramustine Phosphate.

11. Process of claim 10, wherein the salt is transformed to the Estramustine Phosphate in the presence of water and the Estramustine Phosphate is thereafter converted, without isolation, into its alcohol complex.

12. Process of claim 11, wherein the salt is dissolved in water and the solution added to the liquid alcohol-containing phase, which also contains the strong acid.

13. Process of claim 12, wherein the strong acid is hydrochloric acid.

14. Process of claim 2, wherein the precipitated Estramustine Phosphate alcohol complex is dissolved in a solvent other than an alcohol having at least three carbon atoms and selected from the group consisting of alkanols and cycloalkanols and the purified Estramustine Phosphate is precipitated therefrom.

15. Process of claim 14, wherein the solvent is selected from the group consisting of methanol, ethanol, acetonitrile and lower-alkyl lower-alkanoate.

16. Process of claim 2, wherein the precipitated Estramustine Phosphate alcohol complex is dissolved in an organic solvent and an Estramustine Phosphate sodium salt is precipitated therefrom by reacting therewith in solution sodium hydroxide, sodium alcoholate, or a sodium salt of a weak acid.

17. Process of claim 16, wherein the purified Estramustine Phosphate sodium salt is a disodium salt which is precipitated by reacting the Estramustine Phosphate alcohol complex in solution with sodium hydroxide or sodium alcoholate.

18. Process of claim 16, wherein the organic solvent employed is ethanol.

19. A novel Estramustine Phosphate alcohol complex wherein the alcohol has at least three carbon atoms and is selected from the group consisting of alkanols and cycloalkanols.

20. An Estramustine Phosphate alcohol complex of claim 18, wherein the alcohol contains up to a maximum of eight carbon atoms.

21. Complex of claim 20, wherein the Estramustine Phosphate and the alcohol are present in a 1:1 molar ratio.

22. An Estramustine Phosphate alcohol complex of claim 21, wherein the alcohol is selected from the group consisting of secondary and tertiary alcohols.

23. An Estramustine Phosphate alcohol complex of claim 22, wherein the complex is an Estramustine Phosphate propan-2-ol, butan-2-ol, 2-methylpropan-2-ol or cyclohexanol complex.

* * * * *

UNITED STATES PATENT AND TRADEMARK OFFICE
CERTIFICATE OF CORRECTION

PATENT NO. : 4,115,414
DATED : September 19, 1978
INVENTOR(S) : Kristensson et al.

It is certified that error appears in the above-identified patent and that said Letters Patent are hereby corrected as shown below:

[56] References Cited, first reference; "Flex" should read --Fex--

Col. 5, line 36; "tetrahydrofuran;" should read --tetrahydrofurane;--
Col. 5, line 40; "preferred acetone," should read --preferred are acetone,--
Col. 5, line 52; "sovents" should read --solvents--
Col. 6, line 43; "propane" should read --propan--

Signed and Sealed this

Twelfth Day of December 1978

[SEAL]

Attest:

RUTH C. MASON
Attesting Officer

DONALD W. BANNER
Commissioner of Patents and Trademarks